US008058231B2

(12) United States Patent
Ra et al.

(10) Patent No.: US 8,058,231 B2
(45) Date of Patent: Nov. 15, 2011

(54) TRANSCRIPTIONAL REGULATION OF HIGH AFFINITY IGE RECEPTOR γ-CHAIN

(75) Inventors: Chisei Ra, Tokyo (JP); Kyoko Takahashi, Tokyo (JP)

(73) Assignee: Nihon University, Tokyo (JP)

( * ) Notice: Subject to any disclaimer, the term of this patent is extended or adjusted under 35 U.S.C. 154(b) by 625 days.

(21) Appl. No.: 11/992,239

(22) PCT Filed: Sep. 20, 2006

(86) PCT No.: PCT/JP2006/318571
§ 371 (c)(1),
(2), (4) Date: Sep. 24, 2008

(87) PCT Pub. No.: WO2007/043287
PCT Pub. Date: Apr. 19, 2007

(65) Prior Publication Data
US 2009/0054324 A1 Feb. 26, 2009

(30) Foreign Application Priority Data

Sep. 20, 2005 (JP) .................................. 2005-272973

(51) Int. Cl.
| | | |
|---|---|---|
| *C12N 15/11* | (2006.01) | |
| *C12N 15/63* | (2006.01) | |
| *C12Q 1/68* | (2006.01) | |
| *A61K 38/17* | (2006.01) | |
| *C07K 14/47* | (2006.01) | |

(52) U.S. Cl. .......... 514/1.2; 536/235; 435/6; 435/320.1; 530/350

(58) Field of Classification Search ........................ None
See application file for complete search history.

(56) References Cited

U.S. PATENT DOCUMENTS 6,171,803 B1 * 1/2001 Kinet .............................. 435/7.1

OTHER PUBLICATIONS

Küster, H. et al., *Characterization and Expression of the Gene for the Human Fc Receptor γ Subunit*, The Journal of Biological Chemistry, vol. 266, No. 11, Apr. 15, 1990, pp. 6448-6452.
Chisei RA, et al. "A macrophage Fcγ receptor and the mast cell receptor for IgE share an identical subunit", Nature, vol. 341, pp. 752-754, Oct. 26, 1989.

U. Blank, et al. "Complete structure and expression in transfected cells of high affinity IgE receptor", Nature vol. 337, pp. 187-189, Jan. 12, 1989.
Jean-Pierre Kinet, "The High-Affinity IgE Receptor (FcεRI): From Physiology to Pathology", Annu. Rev. Immunol. 1999. 17:931-72.
Hakuoh Konishi, MD, et al. "Platelets Activated by Collagen Through Immunoreceptor Tyrosine-Based Activation Motif Play Pivotal Role in Initiation and Generation of Neointimal Hyperplasia After Vascular Injury", Circulation, pp. 912-916, Feb. 26, 2002.
Yusuke Suzuki, et al. "Distinct contribution of Fc receptors and angiotensin II-dependent pathways in anti-GBM glomerulonephritis", Kidney International, vol. 54 (1998), pp. 1166-1174.
Anna T. Brini, et al. "Involvement of Alu Sequences in the Cell-specific Regulation of Transcription of the γ Chain of Fc and T Cell Receptors", vol. 268, No. 2, Issue of Jan. 15, pp. 1355-1361, 1993.
Takaaki Tamura, et al., "Transcriptional Control Mechanism and Gene Expression," Irasuto Igaku & Scienct Series Tensha no Mechanism to Shikkan, Kabushiki Kaisha Yodosha, Apr. 20, 2000, pp. 12 to 19, Table 2.
Masanari Hasegawa, et al. "Regulation of the Human FcεRI γ-Chain Distal Promoter[1]" The Journal of Immunology., 2003, vol. 170, No. 7, pp. 3732 to 3738.
Robert S. Carter, et al. Cooperative Binding of GA-binding Protein Transcription Factors to Duplicated transcription Initiation Region Repeats of the Cytochrome *c* Oxidase Subunit IV Gene, The Journal of Biological Chemistry, vol. 269, No. 6, Issue of Feb. 11, pp. 4381-4387, 1994.
Activities of the Atopy Research Center, Juntendo University School of Medicine, Apr. 1998-Mar. 2003.
Activities of the Atopy Research Center, Juntendo University School of Medicine, Apr. 1998-Mar. 2003 (*English-language translation of Japanese article submitted in prior IDS*).

* cited by examiner

*Primary Examiner* — Scott Long
(74) *Attorney, Agent, or Firm* — Morgan, Lewis & Bockius LLP (57) ABSTRACT

Transcriptional regulatory regions and transcriptional regulatory factors for the human high affinity IgE receptor (FcεRI) γ-chain gene are specified and are targets for the development of transcriptional regulatory agents for the FcεRI γ-chain gene. The following are provided: DNA comprising the full length or a portion of the base sequence shown in SEQ ID NO:1, that regulates transcription of the human high affinity IgE receptor (FcεRI) γ-chain gene; and DNA comprising the full length or a portion of the base sequence shown in SEQ ID NO:2, that regulates transcription of the human high affinity IgE receptor (FcεRI) γ-chain gene. The present invention is promising for the development of novel agents for the prophylaxis/treatment of allergic diseases, autoimmune diseases, thrombosis, glomerulonephritis, and lupus nephritis.

5 Claims, 5 Drawing Sheets

SEQUENCE LISTING

<160> NUMBER OF SEQ ID NOS: 4

<210> SEQ ID NO 1
<211> LENGTH: 15
<212> TYPE: DNA
<213> ORGANISM: Homo sapiens

<400> SEQUENCE: 1
atgggggaag gcgtg                                                              15

<210> SEQ ID NO 2
<211> LENGTH: 18
<212> TYPE: DNA
<213> ORGANISM: Homo sapiens

<400> SEQUENCE: 2
ggcgtggcag gaagaggg                                                           18

<210> SEQ ID NO 3
<211> LENGTH: 18
<212> TYPE: DNA
<213> ORGANISM: Homo sapiens

<400> SEQUENCE: 3
tctgtggtca gggaactg                                                           18

<210> SEQ ID NO 4
<211> LENGTH: 5131
<212> TYPE: DNA
<213> ORGANISM: Homo sapiens
<220> FEATURE:
<221> NAME/KEY: misc_feature
<222> LOCATION: (614)..(614)
<223> OTHER INFORMATION: n stands for any base
<220> FEATURE:
<221> NAME/KEY: misc_feature
<222> LOCATION: (771)..(771)
<223> OTHER INFORMATION: n stands for any base
<220> FEATURE:
<221> NAME/KEY: misc_feature
<222> LOCATION: (1398)..(1398)
<223> OTHER INFORMATION: n stands for any base
<220> FEATURE:
<221> NAME/KEY: misc_feature
<222> LOCATION: (2515)..(2515)
<223> OTHER INFORMATION: n stands for any base
<220> FEATURE:
<221> NAME/KEY: misc_feature
<222> LOCATION: (2553)..(2553)
<223> OTHER INFORMATION: n stands for any base
<220> FEATURE:
<221> NAME/KEY: misc_feature
<222> LOCATION: (2562)..(2562)
<223> OTHER INFORMATION: n stands for any base
<220> FEATURE:
<221> NAME/KEY: misc_feature
<222> LOCATION: (2585)..(2588)
<223> OTHER INFORMATION: n stands for any base
<220> FEATURE:
<221> NAME/KEY: misc_feature
<222> LOCATION: (2648)..(2650)
<223> OTHER INFORMATION: n stands for any base
<220> FEATURE:
<221> NAME/KEY: misc_feature
<222> LOCATION: (2669)..(2669)
<223> OTHER INFORMATION: n stands for any base
<220> FEATURE:
<221> NAME/KEY: misc_feature
<222> LOCATION: (2956)..(2956)
<223> OTHER INFORMATION: n stands for any base
<220> FEATURE:

```
<221> NAME/KEY: misc_feature
<222> LOCATION: (3105)..(3105)
<223> OTHER INFORMATION: n stands for any base
<220> FEATURE:
<221> NAME/KEY: misc_feature
<222> LOCATION: (4877)..(4877)
<223> OTHER INFORMATION: n stands for any base
<220> FEATURE:
<221> NAME/KEY: misc_feature
<222> LOCATION: (4894)..(4894)
<223> OTHER INFORMATION: n stands for any base
<220> FEATURE:
<221> NAME/KEY: misc_feature
<222> LOCATION: (4908)..(4908)
<223> OTHER INFORMATION: n stands for any base
<220> FEATURE:
<221> NAME/KEY: misc_feature
<222> LOCATION: (4970)..(4970)
<223> OTHER INFORMATION: n stands for any base

<400> SEQUENCE: 4
```

| | | | | | |
|---|---|---|---|---|---|
| atggattcac | ctgagatcag | cagttcaaga | ccagcctgat | caacatggag | aaacccatc | 60 |
| tctactaaaa | atacaaaatt | agctgggcgt | ggtggtgcat | gcctgtaatg | ccagctactc | 120 |
| gggaggctga | gagaatcgct | tgaacctggg | aggcggaggt | tgcggtgagc | cgagatggcg | 180 |
| ccattgcact | ccagcctggg | caacaaagca | agagtccgtc | tcaaaaaaaa | aaaaaaaaa | 240 |
| aaaaatctga | accaggtgga | gtggaaaatg | gcagatgtag | acagccttc | ctgagcgtga | 300 |
| gagtctcctc | attctgtggg | ttaggagttg | gtcattgaag | ggctgacgct | taagagccca | 360 |
| gatctcccaa | ctcccttagt | tggccttccg | ggagccgccc | ggtctcttgt | gcaggaaggg | 420 |
| gaaggggcca | agcatgggg | gaaggcgtgg | caggaagagg | gggactctgt | ggtcagggaa | 480 |
| ctgctcgctg | agcacagctg | cacagtgctg | tcagaacggc | cgatctccag | cccaagatga | 540 |
| ttccagcagt | ggtcttgctc | ttactccttt | tggttgaaca | agcaggtaag | agggtttgtg | 600 |
| agggatagcg | tgantggctc | cagggtgaaa | gtccagagct | tgggtctgag | ggccaagtca | 660 |
| aacacaggtg | aaggaaggct | gacagtgggt | aggtgggcat | agggagaccc | tgaggctagt | 720 |
| cctctccagc | cccgacccag | ggcactagac | tcatagttcc | ctccttcct | nttgccttct | 780 |
| tacttcattc | cagactttc | tccgtattat | tattattatt | ttggagatgg | agtcttgctc | 840 |
| tgtcacccag | gctggagtgc | agtggcgcaa | tctctactca | ctgcaacctc | tgcctcctgg | 900 |
| gttcaagcga | ttctcctgcc | tcaggctccc | gagtagctgg | gactacaggt | gcccgccacc | 960 |
| acgcccggct | aagttaagta | tttttggtag | aaaccgggtt | tcgtcatgtt | gaccagggta | 1020 |
| gtcttgaact | cctgactcaa | gtgatccacc | cacctcgacc | tcccaaagtg | ctgggattac | 1080 |
| tggtgtgagc | cactgcaccc | agctattatt | attattaaaa | aaagacaggg | tcttactatg | 1140 |
| ttggccacat | ccgtcttgaa | ctcctggcct | caagcaattc | tcccacctcg | gcctcccaaa | 1200 |
| gtgctactgt | gcctggctga | cttttctctt | ttcaggggttg | atagaaagtg | gcagggaag | 1260 |
| ggtctggttg | tatggcatga | agagctggtc | tggtgaaacg | cctcatttct | catgatgagc | 1320 |
| atttcccatg | gggtgccttt | ggtcttgtct | gctgggagct | gatctctagc | tggtttaata | 1380 |
| tacaaagcac | ccttggtnct | ataattccag | ctactcagaa | ggctgaggca | ggagaatcac | 1440 |
| ttgaacccag | gaggtggagg | ttgcagtgag | ccaagatcgc | accactgcac | tctagcctgg | 1500 |
| gggacagagt | gagactccgt | ctcaaaaaaa | aaaaaaagat | tttacatata | tatctctatc | 1560 |
| tatctatcta | tatacacaca | cacacacata | cacacacaca | cacacacaca | cacacacaca | 1620 |
| tatatatata | tatagagaga | gagagagaga | gagagagaga | gagagatacc | ctttaggaag | 1680 |
| gtaggactct | gttcttgtgc | ttgggagtaa | ggcaaggata | tagccaagac | aaacagatgg | 1740 |

```
gattgctgtt tctatgggtc attgttaatg ctccattctg tcagcagttg ataatgaggg    1800
tgggcagcat gagatcccca gttccagaga cctgagcgtc agctgagaaa tagaggcaga    1860
aatgggaagg tctctgaagc tctacagctc cagccactat ctaagaattc tcactcctcg    1920
ttcactctgt gttgtctgtg ctggattggt gtgtgtgtgt tggtggcagc tgggtgttgg    1980
ggaggaggag gtcagtaaac ttcagggaaa ctgtgaaatt gaaagagaat gactggggag    2040
gaattccagc agcctagctg agaaggtggg agcaagtatt aagttagcca ctggtctgct    2100
gccgagggat gaggagggag gaggcccgca gaggcacaaa ggaaagcatg ggctttagag    2160
gcagaaaacc tgcatttgag ttccagctct gtcacttaac tctgtggctc tgagtgagtt    2220
acttagcttt tccgagcctt ggtttcgtca cccataaaat ggcgatgatg atgtttccct    2280
cacagggtag ttttaagatt tgtgcaatat cgtgtgtgtg aaagagtgtt gcagaataaa    2340
aagtacttga ccgatgtcag caattgactg acgttagtca catgttccct actggtcctc    2400
tgatacgggg tgagagcagt ctctggagcc cagacttgat ttgattttt aaattgcaca    2460 aaacttcccc tctcagagac ccagagagtg agtaataggg cagagtaaca ggagntggaa    2520
tccatatagc tgtggtcatt cccccagcct tgngttcagg gncaaaggta tctgtaaggt    2580
ctggnnnnaa cagacacact tttttttttt tttttttttt tttacatatt taagtgtctt    2640
gtggtggnnn agaaagcaac aaggctganc taggagatga ccaatgatag agtaattgcc    2700
ttctctccct tccccagctc acatccttcc tgtccagccc tcagccacag gtcacaggac    2760
ttagtagaga cacttctgtg gtttcttcac tgaaatttgc cactacctct ccctcccact    2820
acccatcttg gctgaggttt tggtttcagt ccagtggact cagatgggtc ccttgaggtg    2880
gataaagtgc tcaatggtgc ctgaagaacc cacagtgcta aaaagaaaag gttggggggct   2940 gaggggggaag gcctcnatta ttagtccgtg tgagtcccat ttcaatagaa ccctcaagct    3000
tcctatccta gcctgaccct atggtgtggg aggaggaaa ggtaagggca gtggaaggcc    3060
agagagaaac agaatttctt cccttagacg gctcccctcc aggcnctgtc ctacctccca    3120 gagcccttc ccttctctcc tctgagtacc agatcctccc tgataccccc gaccccatgg    3180
gcatcctcta tcccctcagc ggccctggga gagcctcagc tctgctatat cctggatgcc    3240
atcctgtttc tgtatggaat tgtcctcacc ctcctctact gtcgactgaa ggtagcgctg    3300
ggcagggtgg ggtaagggct ggaagggaa gtggaggag ggcagcagca aggattcgaa    3360
gagaaggaat aaaagggat cctccacaaa gtttggaggg aagggggatg ggccattaac    3420
ttacccttta ctgataaacct ttcccccatt ccagatccaa gtgcgaaagg cagctataac    3480
cagctatgag gtatggaccc tcctacacct ggtgtggaca acttttcaga ccctcagccc    3540
tcctggggct ctagcctggg gtttccgggc tctgggaggg gctgcctctc aggtgctgat    3600
ctgcatacac ctcagaggcc tccctcccac cttacctagc caagccacaa gtaaaatatc    3660
agcaggtgac agggaagaat caagcataga gtgataaaga atatgtgaga gacttggatg    3720
tagtatgtcg ggtgtatatg tgtgcttgta gccatgtggg caaacaggta tcatgtccca    3780
gagtgtccat gtgagtgccc tctagcccaa ggtggctggc tgcccacccc ccatgcctcc    3840
ctgggtgggg cagatgctga ggggccctgg agaaagtgtg ggtctttaat gttttgcttc    3900
ttttgtctct gcagaaatca gatggtgttt acacggtaag tgtgcctacc tcccccaccc    3960
aggaagtcag cagaagaggg tgggattttg agcgatcttt ggaaggccgg tgggggagg     4020 ggggtcctgt ggaggtggga ggggcctctg atggactcca gctcctgatc gcccttttgac   4080 tcccatctcc agggcctgag caccaggaac caggagactt acgagactct gaagcatgag    4140
```

```
aaaccaccac agtagcttta gaatagatgc ggtcatattc ttctttggct tctggttctt    4200
ccagccctca tggttggcat cacatatgcc tgcatgccat taacaccagc tggccctacc    4260
cctataatga tcctgtgtcc taaattaata tacaccagtg gttcctcctc cctgttaaag    4320
actaatgctc agatgctgtt tacggatatt tatattctag tctcactctc ttgtcccacc    4380
cttcttctct tccccattcc caactccagc taaaatatgg gaagggagaa cccccaataa    4440
aactgccatg gactggactc tattcattca ttcattcatt tatcatagat ttattcagtc    4500
tctgctaagc actagataca gcttttcagt tccagaactc acagtctaat ggacttcaga    4560
gctattttgc tcgactgagg gataaatgct gactatggct gggggaggga taaaaacctt    4620
tgacctgtag gtgctctgag gatggagctg gagcagggac tagtgtgttg ggagtctagg    4680
catatttgga aacataagaa atgacttctg tatcagcatg ccttctgtgt tcgacaattg    4740
aaccaggttg ggttgtaggg gaggtgggtg tccagatggc accaatcaga cagcatgatc    4800
agtcatcata tgggattgct gctgaaagca aatatcagac gatggtgtac tgggctgggt    4860
gagctctatg gaggttnttg ggcaagtggg accnttagag ggccagantg ggtcagtggt    4920
aggtaaggca aagggaaata agttgggtcc aaatgggggg gtcatctccn ttcaagtgca    4980
tgggtggtgg tcaaggccct tgttcaatgc ctgttcctgt ttttcagagc tacgaggaat    5040
atttgcctga aagaatttaa acctcaggag atgctgccag tcctactcgt gacccagttc    5100
ttttcagaat gggtctagag actccaagct t                                   5131
```

TRANSCRIPTIONAL REGULATION OF HIGH AFFINITY IGE RECEPTOR γ-CHAIN

FIELD OF THE INVENTION

The present invention relates to the regulation of the expression of the high affinity IgE receptor γ-chain and more particularly relates to transcriptional control of the high affinity IgE receptor γ-chain gene and to the utilization of this transcriptional control.

BACKGROUND

The high affinity IgE receptor (referred to below as FcεRI) expressed on the cell membrane of mast cells and basophils is known to be a key glycoprotein in the type I allergic reaction. When antigen-specific IgE's bonded to FcεRI are crosslinked by the corresponding polyvalent antigen (for example, cedar pollen antigen for individuals suffering from cedar pollen allergy, dust mite antigen for individuals suffering from dust mite allergies), the FcεRI's are clustered, the signal transduction mechanism operates, and the mast cells undergo initial activation. As a result, various chemical transmitters that evoke allergic inflammation, i.e., most prominently the histamine preliminarily stored in cell granules, are released and the new synthesis and release of leukotriene, prostaglandin, and so forth, which are intracellular metabolites, is explosively induced, evoking a type I allergic reaction.

In addition, cytokine secretion from mast cells is promoted by the clustering of FcεRI's on the mast cells, inducing the expression of various adhesion molecules in the neighboring vascular endothelial cells. Eosinophils and lymphocytes in the blood aggregate by binding via these adhesion molecules to the vascular endothelial cells at the site of inflammation. The late allergic reaction is evoked as a result. Moreover, the FcεRI expressed by the Langerhans cells of the skin is presumed to contribute to the pathogenesis of atopic dermatitis by antigen presentation and cytokine production.

Based on the preceding, a promising strategy for the development of agents for allergy prophylaxis treatment is to target the FcεRI that specifically mediates type I allergy and thereby block signal transduction from this receptor at the point of origin.

FcεRI is also known to participate in platelet activation and glomerulonephritis, and given this it is also promising to carry out the development of thrombosis and glomerulonephiritis by targeting FcεRI.

In humans, human FcεRI functions expressed on the cell surface as a tetramer of an α-chain, a β-chain, and 2 γ-chains or as a trimer of an α-chain and 2 γ-chains. The extracellular region of the α-chain binds-directly to IgE while the β-chain γ-chain participate in signal transduction into the cell. The γ-chain assembles with the other molecules, which have a ligand binding site, to form a receptor on the cell surface. When ligand binds to the receptor's ligand binding site, the γ-chain transduces the signal into the cell.

For example, the γ-chain has been reported to perform the function of transmitting an activation signal into the cell in the FcεRI-mediated induction of allergic reactions (refer, for example, to Non-Patent documents 1 to 3). In addition, the γ-chain has been reported to induce the platelet activation reaction by associating with the collagen receptor GP VI on the platelet (refer, for example, to Non-Patent document 4). The γ-chain is also a constituent element of the IgG receptors FcγRIII and FcγRI and the IgA receptor FcαR, and the suggestion has also been made these FcR's participate in glomerulonephritis-(refer, for example, to Non-Patent document 5).

Non-Patent document 1 Ra C et al., Nature, 341:752-754 (1989);
Non-Patent document 2 Blank U et al., Nature, 337; 187-189 (1989);
Non-Patent document 3 Kinet J P, Annual Review of Immunology, 17:931-972 (1999);
Non-Patent document 4 Konishi H et al., Circulation, 105(8): 912-916 (2002);
Non-Patent document 5 Suzuki Y et al., Kidney Int., 54(4): 1166-1174 (1998)

However, on the subject of transcriptional regulatory regions for the high affinity human IgE receptor γ-chain, only the analysis by Brini A T et al., in 1993 has been carried out, and to date no detailed analysis that precisely identifies transcriptional regulatory elements and/or transcriptional regulatory factors has been performed.

As a result of intensive investigations, the present inventors succeeded in identifying, from within previously unanalyzed regions, regions that participate in the transcriptional regulation of the human FcεRI γ-chain gene and in identifying transcription factors that bind to these regions and were thereby able to achieve the present invention.

SUMMARY

That is, the present invention provides (1) a DNA comprising the full length or a portion of the base sequence shown in SEQ ID NO:1, that regulates transcription of the human high affinity IgE receptor (FCεRI) γ-chain gene; (2) a method of regulating transcription of the FcεRI γ-chain gene, that regulates the binding of Sp1 with an FcεRI γ-chain gene transcriptional regulatory region comprising the full length or a portion of the base sequence shown in SEQ ID NO:1; (3) a method of screening for a compound, or salt thereof, that regulates the binding of Sp1 with an FcεRI γ-chain gene transcriptional regulatory region comprising the full length or a portion of the base sequence shown in SEQ ID NO:1; (4) a DNA comprising the full length or a portion of the base sequence shown in SEQ ID NO:2, that regulates transcription of the human high affinity IgE receptor (FcεRI) γ-chain gene; (5) a method of regulating transcription of the FcεRI γ-chain gene, that regulates the binding of Elf-1 or GABP α/β heterodimer with an FcεRI γ-chain gene transcriptional regulatory region comprising the full length or a portion of the base sequence shown in SEQ ID NO:2; (6) a method of screening for a compound, or salt thereof, that regulates the binding of Elf-1 or GABP α/β heterodimer with an FcεRI γ-chain gene transcriptional regulatory region comprising the full length or a portion of the base sequence shown in SEQ ID NO:2; (7) a DNA comprising the full length or a portion of the base sequence shown in SEQ ID NO:3, that regulates transcription of the human high affinity IgE receptor (FcεRI) γ-chain gene; (8) a method of regulating transcription of the FcεRI γ-chain gene, that regulates the binding of C/EBP with an FcεRI γ-chain gene transcriptional regulatory region comprising the full length or a portion of the base sequence shown in SEQ ID NO:3; (9) a method of screening for a compound, or salt thereof, that regulates the binding of C/EBP with an FcεRI γ-chain gene transcriptional regulatory region comprising the full length or a portion of the base sequence shown in SEQ ID NO:3. (10) a method of regulating transcription of the human high affinity IgE receptor (FcεRI) γ-chain gene by controlling functional regulation by at least one transcription factor selected from Sp1, Elf-1, GABP α/β heterodimer, and C/EBP or by controlling the interaction between or among transcription factors; (11) a vector that incorporates the full length or a portion of the base sequence shown in SEQ ID NO:1, SEQ ID NO:2, or SEQ ID NO:3; (12) a screening kit used in the screening method according to the preceding (3), (6), or (9); (13) a drug containing a compound, or salt thereof, that regulates transcription of the FcεRI γ-chain gene and is obtained using the screening method according to the preceding (3), (6), or (9) or the transcriptional regulatory method according to the preceding (10); (14) the drug described in the preceding (13), that is a prophylactic/therapeutic agent for allergic diseases or autoimmune diseases; (15) the drug described in the preceding (13), that is a prophylactic/therapeutic agent for thrombosis; and (16) the drug described in the preceding (13), that is a prophylactic/therapeutic agent for glomerulonephritis or lupus nephritis.

Thus, the present inventors cloned the human γ-chain gene and using a human cell line carried out a reporter assay on the region upstream from the translation initiation point. The presence of two enhancer elements in the nt-103/-75 region (here and in the following, the translation initiation point is designated as base number +1) was elucidated as a result, i.e., the region shown by SEQ ID NO:1, containing nt-98 to -96, and the region shown by SEQ ID NO:2, containing nt-84 to -82. With regard to these elements, it was found by EMSA that Sp1 binds to the former and that Elf-1 or GABP α/β heterodimer binds to the latter.

In addition, the region of SEQ ID NO:3, which contains nt-65 to -61 and exhibits homology with the C/EBP binding sequence, was found to contribute to activation of the γ-chain promoter. On the occasion of carrying out reporter assays while inducing overexpression of various combinations of these transcription factors, it was shown that transcription activation was synergistically increased and that the use of a plurality of the transcription factors resulted in cooperative activation of the γ-chain promoter.

Moreover, in view of the following facts as cited in the preceding: the γ-chain functions to transmit the activation signal into the cell during induction of the FcεRI-mediated allergic reaction, the γ-chain induces the platelet activation reaction by associating with the collagen receptor GP VI on the platelet, and the γ-chain is a constituent element of the IgG receptors FcγRIII and FcγRI and the IgA receptor FcαR and these FcR's participate in the pathogenesis of glomerulonephritis, the expression regulatory regions and control factors identified by the present inventors for the γ-chain gene are useful as targets for the development of prophylactic/therapeutic agents for, inter alia, allergic diseases, autoimmune diseases, thrombosis, glomerulonephritis, and lupus nephritis. The present invention is also useful for genetic analysis in personalized medicine.

The genomic structure and base sequence of the human FcεRI γ-chain gene have already been elucidated (GenBank, accession number M33196, SEQ ID NO:4). The phrase, "comprising the full length or a portion of the base sequence shown in SEQ ID NO:1", used in the present invention means comprising the main portion essential for transcriptional regulation of the FcεRI γ-chain gene and in particular comprising a sequence based on nt-98 to -96 (the translation initiation point is designated as base number +1).

The phrase, "comprising the full length or a portion of the base sequence shown in SEQ ID NO:2", used in the present invention means comprising the main portion essential for transcriptional regulation of the FcεRI γ-chain gene and in particular comprising a sequence based on nt-84 to -82 (the translation initiation point is designated as base number +1).

The phrase, "comprising the full length or a portion of the base sequence shown in SEQ ID NO:3", used in the present invention means comprising the main portion essential for transcriptional regulation of the FcεRI γ-chain gene and in particular comprising a sequence based on nt-65 to -61 (the translation initiation point is designated as base number +1).

The "high affinity IgE receptor γ-chain" referenced in the present invention was discovered as a high affinity IgE receptor γ-chain, but subsequent findings have shown that, inter alia, other immunoglobulin Fc receptors also contain it in common as a constituent element, and at the present time it is also known as "immunoglobulin receptor γ-chain".

The present invention provides base sequences that participate in transcriptional regulation of the human FcεRI γ-chain gene and establishes a method of screening for compounds and salts thereof that inhibit γ-chain expression and also establishes a kit for use in this screening method.

DETAILED DESCRIPTION

Embodiments of the present invention will now be described. The following embodiments are examples for the purpose of explaining the present invention, but the present invention should not be construed as limited only to these embodiments. The present invention can be implemented using various modalities while preserving the essential features of the present invention.

The present invention, based on the determination of DNA regions that participate in regulating transcription of the FcεRI γ-chain gene and the identification of transcriptional regulatory factors that bind to these regions, enables the construction of a method of screening for compounds and salts thereof that inhibit expression of the FcεRI γ-chain and of a kit for use in this screening. The present invention thereby contributes to the development of agents for the prophylaxis or treatment of allergic diseases, autoimmune diseases, thrombosis, glomerulonephritis, and lupus nephritis. For example, the development of compounds or salts thereof that inhibit γ-chain expression is possible based on the strategy of searching for substances that inhibit the binding of the identified transcriptional regulatory factor Sp1 with the specified gene region.

The aforementioned salt of a compound denotes, inter alia, a salt with a physiologically acceptable acid (for example, an inorganic acid or an organic acid) or a salt with a physiologically acceptable base (for example, an alkali metal). Physiologically acceptable acid-adduct salts are particularly preferred. Specific examples are salts with hydrochloric acid, phosphoric acid, hydrobromic acid, and sulfuric acid within the realm of inorganic acids and salts with acetic acid, formic acid, propionic acid, fumaric acid, maleic acid, succinic acid, tartaric acid, citric acid, malic acid, oxalic acid, benzoic acid, methanesulfonic acid, benzenesulfonic acid, and so forth within the realm of organic acids.

An FcεRI γ-chain gene transcription-regulating compound or salt thereof that is obtained using the screening method and screening kit according to the present invention is useful as an agent for the prophylaxis/treatment of allergic diseases, autoimmune diseases, thrombosis, glomerulonephritis, and lupus nephritis.

A compound or salt thereof obtained by means of the present invention can be used via the oral route as, for example, a tablet or pill, possibly sugar coated, a capsule, or a microcapsule, or can be used via a parenteral route in the form of an injectable, for example, a sterile solution or suspension with water or with a pharmaceutically acceptable liquid other than water. For example, production can be carried out by mixing a compound or salt thereof obtained by means of the present invention, in the unit dose form required for the elaboration of a generally recognized formulation, with, for example, a physiologically acceptable carrier, flavorant, filler, vehicle, preservative, stabilizer, binder, and so forth.

The amount of effective component in these formulations is an amount that provides an appropriate dose in the indicated range. Additives that can be incorporated into, for example, a tablet or capsule, can be exemplified by binders such as gelatin, corn starch, tragacanth, gum arabic, and so forth; fillers such as crystalline cellulose; swelling agents such as corn starch, gelatin, alginic acid, and so forth; lubricants such as magnesium stearate and so forth; sweeteners such as sucrose, lactose, saccharin and so forth; and flavorants such as peppermint, Japanese wintergreen (*Gaultheria adenothrix*) oil, and cherry. When the unit formulation takes the form of a capsule, starting material of the aforementioned type may also include a liquid carrier such as an oil or fat. Sterile compositions for injection can be formulated by the usual methods for producing a formulation, such as dissolving or suspending a natural vegetable oil or the like, such as sesame oil or coconut oil, and the active ingredient in a vehicle such as injection-grade water.

Examples of aqueous solutions for use as injection-grade water include physiological saline, isotonic solutions containing glucose and/or other adjuvants (such as D-sorbitol, D-mannitol, sodium chloride, and so forth), and suitable dissolution auxiliaries such as alcohols (e.g., ethanol), polyalcohols (e.g., propylene glycol, polyethylene glycol, and so forth), and nonionic surfactants (e.g., Polysorbate 80™, HCO-50, and so forth) can be used in combination therewith. Sesame oil and soy oil are examples of dissolution auxiliaries, and, for example, benzyl benzoate, benzyl alcohol, and so forth can be used in combination therewith as dissolution auxiliaries. Buffers (e.g., phosphate buffers, sodium acetate buffers, and so forth), analgesics (e.g., benzalkonium chloride, procaine chloride, and so forth), stabilizers (e.g., human serum albumin, polyethylene glycol, and so forth), preservatives (e.g., benzyl alcohol, phenol, and so forth), antioxidants, and the like may also be incorporated. The formulated injectable is usually filled into a suitable ampule.

A formulation obtained as described in the preceding is safe and exhibits low toxicity and can therefore be administered to, for example, mammals and warm-blooded animals (for example, human, rat, mouse, guinea pig, rabbit). The administered dose of a compound or salt obtained by means of the present invention will vary as a function of, inter alia, the targeted disease, the recipient of the administration, and the route of administration. As an example, when a compound or salt thereof obtained by means of the present invention is administered orally for the purpose of treating hay fever, 0.1 mg to 1.0 g and preferably about 1.0 mg to 50 mg of the compound or salt thereof is generally administered per day to an adult (60 kg).

EXAMPLES

The present invention is described in additional detail in the following using examples, but the present invention is not limited to these examples. The individual skilled in the art will be able to implement not only the examples given in the following, but will also be able to add various modifications; these modifications are also encompassed in the claims provided herein.

Example 1

Measurement of the Transcriptional Regulatory Activity of the 5' Region of the Human FcεRI γ-chain Gene nt-103 to -1 and nt-74 to -1 at the 5' region of the human FcεRI γ-chain gene were each incorporated upstream from the luciferase gene in the pGL3Basic Vector (Promega), a plasmid that contains the firefly luciferase gene as a reporter gene, to construct the respective reporter plasmids. 5 μg of the particular reporter plasmid and 0.1 μg pRL-CMV Vector (Promega), a plasmid encoding the *Renilla* luciferase gene under CMV promoter control, as the control were transfected into each of four γ-chain-expressing human cell lines (Jurkat, KU812, THP1, U937) by electroporation (300 V, 950 μF).

After cultivation for 20 to 24 hours at 37° C./5% $CO_2$, the cells were recovered and cell lysis and measurement of the luciferase activity were carried out using a Dual Luciferase Assay Kit (Promega). At the time of measurement, the value of firefly luciferase activity/*Renilla* luciferase activity was calculated for each sample and the plasmid transfection efficiency and cell lysis efficiency were corrected.

Figure 1:
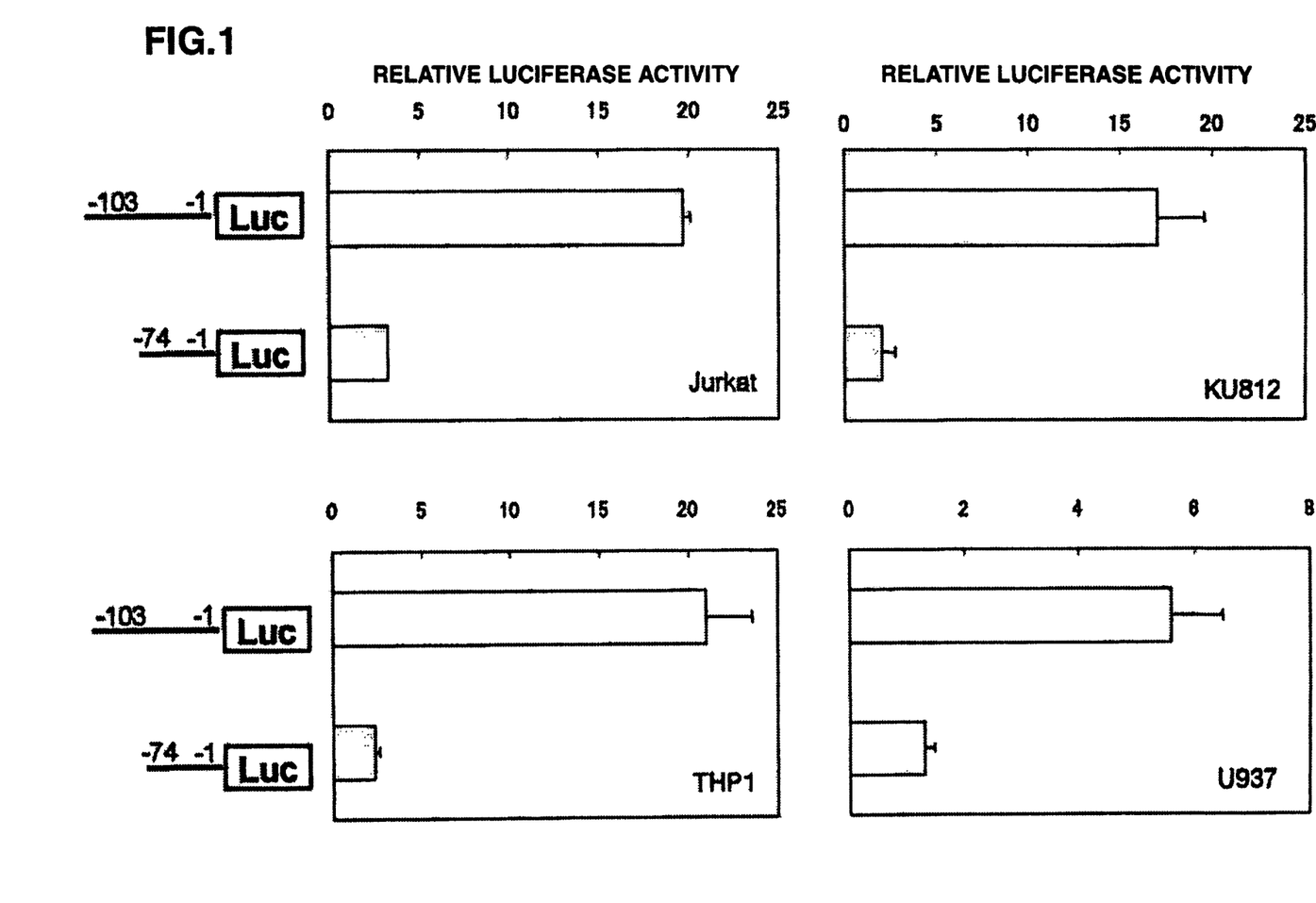
FIG. 1 shows the transcriptional regulatory activity according to a reporter assay of the 5' region of the human FcεRI γ-chain gene.

The relative activity is shown in FIG. 1, where a value of 1 was assigned to the luciferase activity for transfection with a reporter plasmid containing only the firefly luciferase gene. As shown in FIG. 1, in all of the γ-chain-expressing cell lines used, the -103 to -1 region caused a major enhancement in luciferase activity, while the -74 to -1 region showed almost no enhancement effect of this nature. This example demonstrated that a transcription activating element with a common function in the four cell lines is present in the -103 to -75 region.

Example 2

Identification of Factors Binding to nt-102 to -88

Gel shift assays were carried out using a nuclear extract prepared from KU812 cells and the FITC-labeled double-stranded synthetic oligoDNA probe 5'-ATGGGGGAAG-GCGTG-3' (corresponds to nt-102/-88 of the γ-chain gene).

Two unlabeled double-stranded synthetic oligoDNA's were used as the competitors: one having the same base sequence as the probe (comp) and one in which the three bases at nt-98 to -96 were changed (mut-comp).

30 μl of the aforementioned nuclear extract and 5 pmol of the aforementioned probe and 25 or 250 pmol of the competitor were mixed in a 10 mM HEPES buffer (pH 7.9) containing 400 ng poly(dI-dC), 1 mM MgCl$_2$, 30 mM KCl, 1 mM DTT, and 5% glycerol and this was allowed to stand for 20 minutes at room temperature. This was followed by submission to 4% polyacrylamide gel electrophoresis using 0.5×TBE buffer (45 mM Tris, 45 mM boric acid, 1 mM EDTA). After phoresis for 2 to 3 hours at 120 V, the FITC fluorescence was detected using a FluorImager 595 (Amersham Bioscience). The results are shown in FIG. 2(A).

Figure 2A:
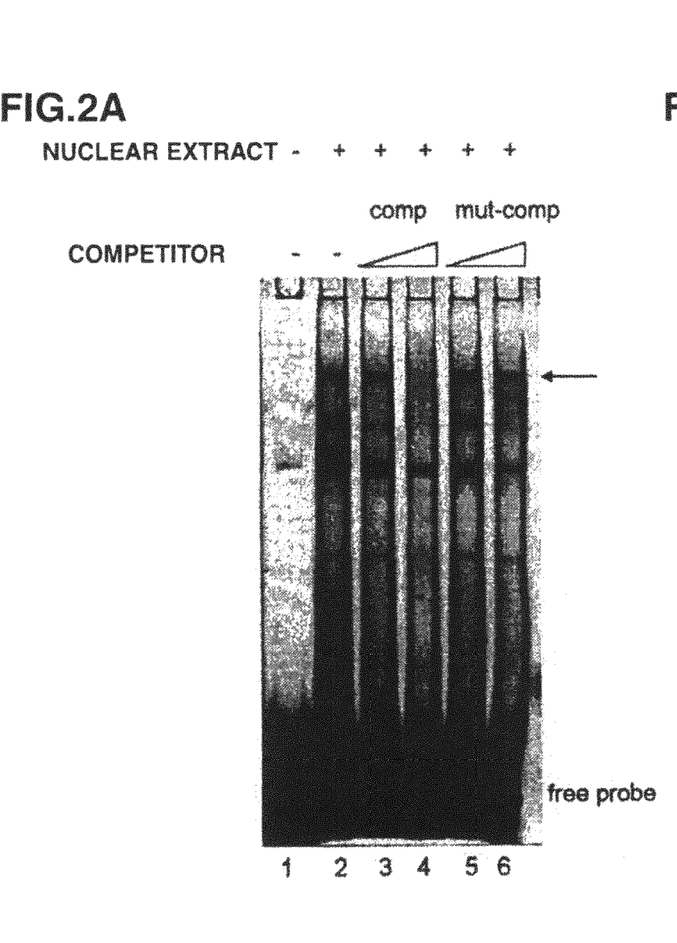
FIG. 2 shows the identification of binding factors by a gel shift assay, wherein (A) is a competitive test using unlabeled double-stranded oligoDNA (the added unlabeled double-stranded DNA was as follows: lanes 3, 4; sequence identical to probe, lanes 5, 6; three bases substituted in the probe sequence) and (B) is a test using antibody.

As shown in FIG. 2(A), several bands were observed (lane 2) that were shifted to positions of lower mobility than the band for the probe by itself. Among these, the band indicated by the arrow was extinguished in a competitor concentration-dependent manner when comp was added at 25 and 250 pmol (lanes 3 and 4), while extinction of this band did not occur in the case of the addition of mut-comp at 25 and 250 pmol (lanes 5 and 6). This showed that this band was a band in which nuclear protein was bound with specific recognition of the sequence based on nt-98 to -96.

The same results were obtained for the use of nuclear extracts prepared from Jurkat, THP1, and U937.

Figure 2B:
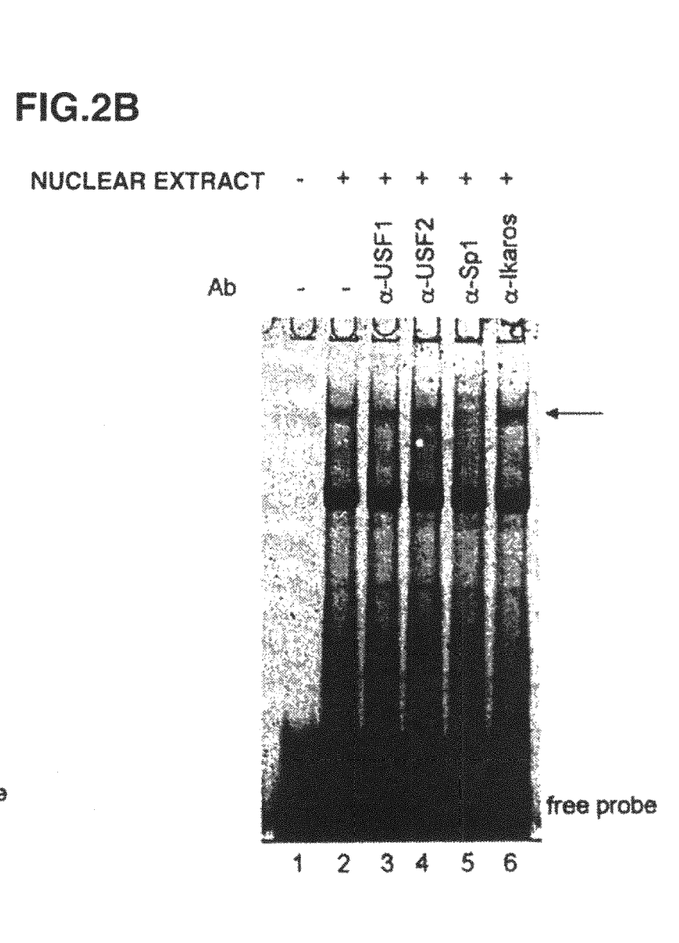

In order to identify this nuclear protein, 2 μg antibody (Santa Cruz Biotechnology, Inc.) against each of the transcription factors USF-1, USF-2, Sp1, and Ikaros was added. As shown in FIG. 2(B), the band indicated by the arrow was extinguished only for the addition of anti-Sp1 antibody. The same results were obtained for the use of nuclear extracts prepared from Jurkat, THP1, and U937. It was thus confirmed that the transcription factor Sp1 binds to the sequence based on nt-98 to -96.

Example 3

Identification of Factors Binding to nt-93 to -76

In order to identify factors binding to nt-93 to -76 of the human FcεRI γ-chain gene, a gel shift assay was carried out as in Example 2, but in this case using the double-stranded synthetic oligoDNA probe 5'GGCGTGGCAGGAA-GAGGG-3' as the probe and using, as the competitors, two unlabeled double-stranded synthetic oligo's, one having the same base sequence as the probe (comp) and one in which the three bases at nt-84 to -82 were changed (mut-comp). The results are shown in FIG. 3(A).

Figure 3A:
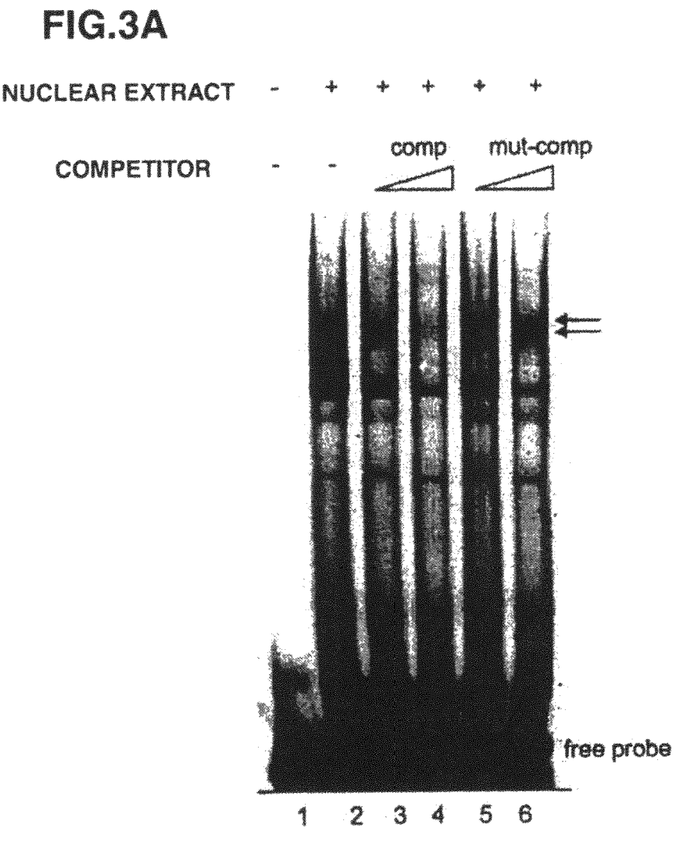
FIG. 3 shows the identification of binding factors by a gel shift assay, wherein (A) is a competitive test using unlabeled double-stranded oligoDNA (the added unlabeled double-stranded DNA was as follows: lanes 3, 4: sequence identical to probe, lanes 5, 6: three bases substituted in the probe sequence) and (B) is a test using antibody.

As shown in FIG. 3(A), the two bands indicated by the arrows underwent a competitor concentration-dependent extinction in the case of the addition of 25 and 250 pmol comp (lanes 3 and 4), but were not extinguished in the case of the addition of 25 and 250 pmol mut-comp (lanes 5 and 6). This showed that these bands were bands in which nuclear protein was bound with specific recognition of the sequence based on nt-84 to -82. The same results were obtained for the use of nuclear extracts prepared from Jurkat, THP1, and U937.

Figure 3B:
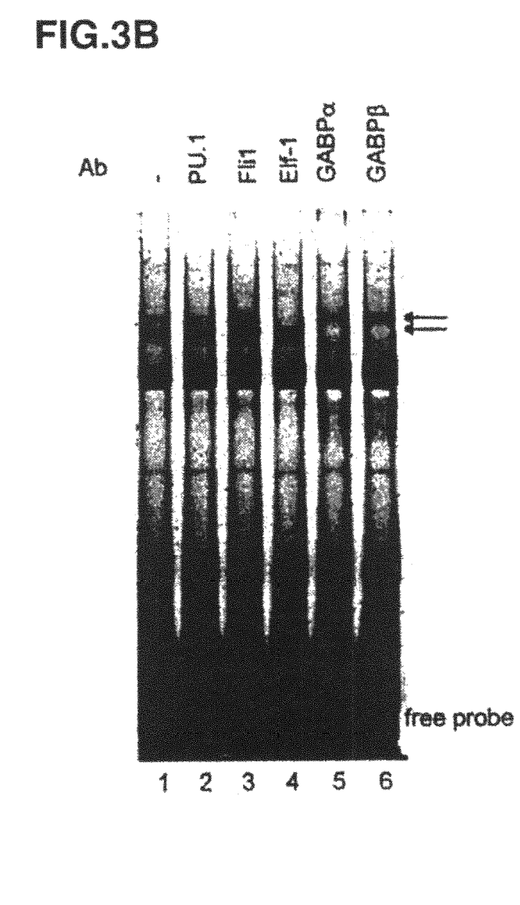

In order to identify this nuclear protein, 2 μg antibody (Santa Cruz Biotechnology, Inc.) against each of the transcription factors PU.1, Fli1, Elf-1, GABP α, and GABP β was added. As shown in FIG. 3(B), of the two bands indicated by the arrows, the lower band was extinguished when anti-GABP α antibody and anti-GABP β antibody were added, while the upper band was extinguished by the addition of anti-Elf-1 antibody. The same results were obtained for the use of nuclear extracts prepared from Jurkat, THP1, and U937. It was thus confirmed that GABP α/β heterodimer and Elf-1 bound to the sequence based on nt-84 to -82.

Example 4

Figure 4:
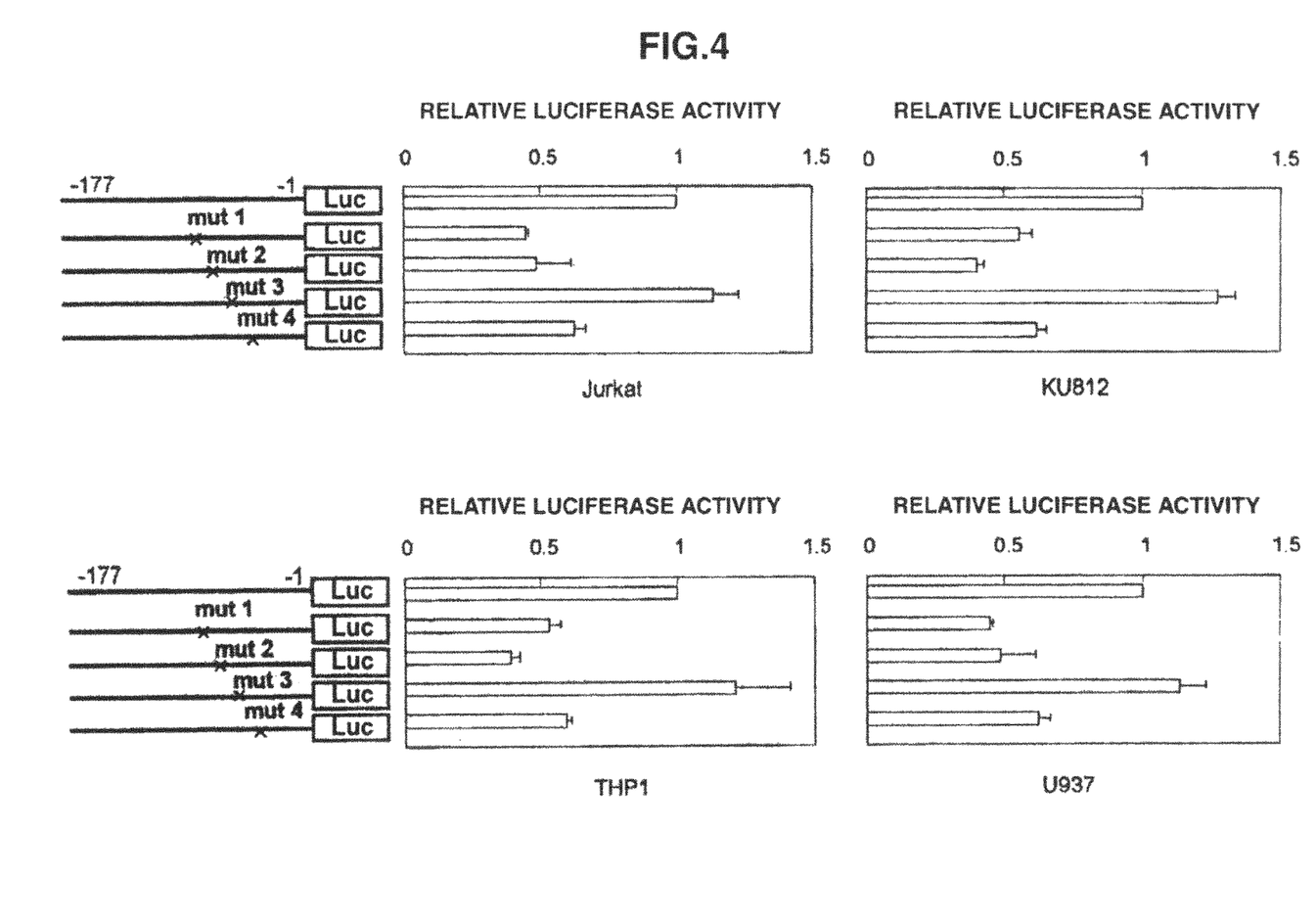
FIG. 4 shows the effect of site-directed mutagenesis on human FcεRI γ-chain gene promoter activity.

Influence of Base Substitution by Site-directed Mutagenesis on γ-chain Promoter Activity The nt-177 to -1 fragment of the human FcεRI γ-chain gene was inserted upstream from the firefly luciferase gene in the pGL3Basic Vector (Promega), and the γ-chain gene fragment in the resulting plasmid was subjected to site-directed mutagenesis to construct four reporter plasmids. Thus, using a Quick Change Site-Directed Mutagenesis Kit (Stratagene), four reporter plasmids were obtained by replacing the following three or four bases, respectively: nt-98 to -96 (mut1), -84 to -82 (mut2), -77/-75/-74 (mut3), and -65/-64/-62/-61 (mut4). Proceeding as in Example 1, expression testing was carried out by transfecting the obtained reporter plasmids into human cell lines (Jurkat, KU812, THP1, U937). The relative activity is shown in FIG. 4, where a value of 1 was assigned to the luciferase activity for transfection with the reporter plasmid in which mutation had not been induced. As shown in FIG. 4, a decline in luciferase activity was observed for base substitution at nt-98 to -96, -84 to -82, and -65/-64/-62/-61, while the luciferase activity was unchanged for base substitution at -77/-75/-74.

The regions based on nt-98 to -96 and -84 to -82, which were shown in accordance with the preceding Examples 2 and 3 to bind, respectively, Sp-1 and GABP α/β or Elf-1, were confirmed in accordance with this example to function as transcription activation elements. In addition, the region based on nt-65 to -61, which is downstream from the preceding, was also shown to function as a transcription activation element. The region based on nt-65 to -61 is homologous with the binding motif of the C/EBP transcription factor. Moreover, when these results are considered in combination with the results of Example 1, the conclusion is drawn that this element has almost no transcription activating capacity by itself and functions cooperatively with the other two transcription activation elements.

Example 5

Influence of the Overexpression of Various Transcription Factors on γ-chain Promoter Activity Expression tests were carried out as in Example 1 by transfecting HeLa cells with 5 μg of a reporter plasmid prepared by inserting the nt-177 to -1 region of the human FcεRI γ-chain gene upstream from the firefly luciferase gene in the pGL3-Basic Vector (Promega) and with 3 μg of an expression plasmid for GABP α, GASP β, Elf-1, Sp1, and/or C/EBP α.

Figure 5:
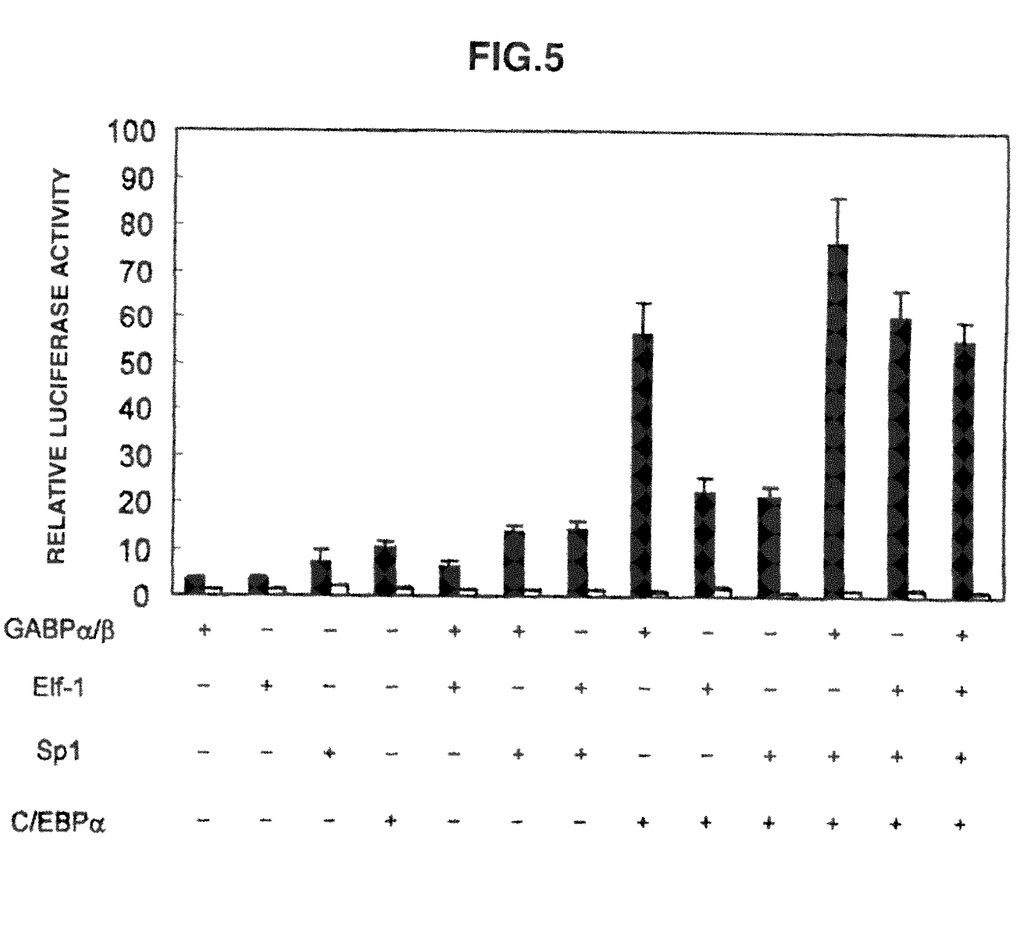
FIG. 5 shows the effect of the overexpression of the different transcription factors on human FcεRI γ-chain gene promoter activity in HeLa cells.

The relative activity is shown in FIG. 5, where a value of 1 is assigned to the luciferase activity for transfection with only the reporter plasmid. The black bar in the graph in FIG. 5 shows the relative activity for transfection with the expression plasmid(s) for the particular transcription factor(s), while the white bar shows the relative activity for transfection with the same amount of the corresponding empty vector. As shown in FIG. 5, the luciferase activity was increased several fold by the expression of GASP α/β only, or Elf-1 only, or Sp1 only, or C/EBP α only, in comparison to transfection with the empty vector, thus confirming that these transcription factors in fact activate the γ-chain promoter. In addition, a synergistic activation of the γ-chain promoter was shown for GABP α/β+Sp1+C/EBP α and for Elf–1+Sp1+C/EBP α.

We claim:

1. An isolated nucleic acid molecule consisting of the nucleotide sequence of SEQ ID NO:1.

2. A method of screening for a compound, or salt thereof, that regulates the binding of Sp1 with an FcεRI γ-chain gene transcriptional regulatory region comprising,
   contacting the compound with the isolated nucleic acid molecule of claim 1, and
   selecting a sample that binds to the isolated nucleic acid molecule wherein the presence of binding indicates that the compound regulates the binding of Sp1 with an FcεRI γ-chain gene transcriptional regulatory region.

3. A screening kit comprising the isolated nucleic acid molecule of claim 1.

4. The nucleic acid molecule of claim 1, wherein the nucleic acid molecule regulates transcription of the human high affinity IgE receptor (FcεRI) γ-chain gene.

5. The method of claim 2, wherein the method utilizes a gel shift assay or an antibody assay.

* * * * *